United States Patent
Gorsek

(10) Patent No.: US 6,936,286 B2
(45) Date of Patent: Aug. 30, 2005

(54) HEALTHY BONE FORMULATION

(75) Inventor: Wayne F. Gorsek, Boynton Beach, FL (US)

(73) Assignee: Vitacost.com, Inc., Boynton Beach, FL (US)

(*) Notice: Subject to any disclaimer, the term of this patent is extended or adjusted under 35 U.S.C. 154(b) by 623 days.

(21) Appl. No.: 10/187,616

(22) Filed: Jul. 3, 2002

(65) Prior Publication Data

US 2004/0005366 A1 Jan. 8, 2004

(51) Int. Cl.[7] .......................... A01K 35/78; A61K 9/20; A61K 33/00
(52) U.S. Cl. ...................... 424/757; 424/725; 424/600; 424/682; 424/764; 424/464
(58) Field of Search ................. 424/725, 757, 424/600, 682, 764, 464, 602

(56) References Cited

U.S. PATENT DOCUMENTS 6,139,872 A * 10/2000 Walsh ........................ 424/464
6,436,446 B1 * 8/2002 Forusz et al. ............... 424/682

OTHER PUBLICATIONS

Balch et al. Prescription for Nutritional Healing; 2nd Ed. (1997) pp. 417–418.*

* cited by examiner

Primary Examiner—Patricia Leith
(74) Attorney, Agent, or Firm—Hoffman, Wasson & Gitler, P.C.

(57) ABSTRACT

The key to the unique formulation is a combination of specific vitamins, minerals, herbs and nutrients. These essential components in the amounts provided uniquely contribute to improved bone mass and reduction of bone fracture rates. The formulation contains essential amounts of calcium, magnesium Vitamin D, Vitamin K-1, Folic Acid and Soy Isoflavones, as well as other ingredients and healthy filler components.

2 Claims, No Drawings

HEALTHY BONE FORMULATION

BACKGROUND OF THE INVENTION

The invention relates to a composition that contains the most potent combination of nutrients with clinical studies proven to assist in the maintenance of normal bone density and development.

The advanced formulation is designed to reduce bone loss and reduce bone fracture rates by significant amounts. It helps in the treatment and prevention of osteoporosis and osteoarthritis.

It is estimated that between 37 to 50 million people in this country suffer with some degree of bone loss. An unique and effective combination of minerals and supplements are required to prevent such loss and deterioration.

It is an object of the present invention to provide an unique formulation which allows individuals improve, bone strength and reduce age related deterioration and fracture problems due to loss of bone density.

SUMMARY OF THE INVENTION

The key to the unique formulation is a combination of specific vitamins, minerals, herbs and nutrients. These essential components in the amounts provided uniquely contribute to improved bone mass and reduction of bone fracture rates.

The formulation contains essential amounts of Calcium, Magnesium, Vitamin D, Vitamin K-1, Folic Acid and Soy Isoflavones, as well as other ingredients and healthy filler components.

The formulation is preferably delivered in capsule form at 4 capsules per day.

DETAILED DESCRIPTION OF THE INVENTION

The present invention involves a composition for oral ingestion that contains The formulation contains essential amounts of Calcium, Magnesium, Vitamin D, Vitamin K-1, Folic Acid and Soy Isoflavones, as well as other ingredients and healthy filler components. More specifically, this formulated product is a maintenance formualtion for preservation of bone density and reduction fo bone fracture rates. This formulation allows for a significant reduction in bone fracture rates and allows for prevention and treatment of osteoporosis.

In order to secure the desired result the following essential components are provided:

Calcium (from 2,278 mg citate, malate) in an amount of approximately 500 mg (50 mg–5,000 mg).

Magnesium (from 1191 mg citate) in an effective amount of 250 mg (25 mg–2,500 mg).

Vitamin D (as cholecalciferol) in an effective amount of approximately 700 IU (70 IU–7,000 IU).

Vitamin K-1 (Phytonadione) in an effective amount of approximately 150 mcg (15 mcg–1,500 mcg).

Folic Acid is an amount of approximately 800 mcg (80 mcg–8,000 mcg).

Soy isoflavones (standardized to 40%) (100 mg) (10 mg–1,000 mg)

In addition to the key components, other components such as kosher gelatin (capsules), magnesium stearate and silica and cellulose are included.

Although the invention has been described primarily in connection with special and preferred embodiments, it will be understood that it is capable of modification without departing from the scope of the invention. The following claims are intended to cover all variations, uses, or adaptations of the of the invention, following, in general the principles thereof and including such departures from the present disclosure as come within known or customary practice in the field to which the invention pertains, or as are obvious to persons skilled in the field.

What is claimed is:

1. A healthy bone maintenance composition comprising an effective amount of:

Calcium;

Magnesium;

Vitamin D;

Vitamin K-1;

Folic Acid; and

Soy Isoflavones.

2. A healthy bone maintenance composition comprising an effective amount of approximately:

500 mg Calcium;

250 mg Magnesium;

700 IU Vitamin D;

150 mcg Vitamin K-1;

800 mcg Folic Acid; and 100 mg Soy Isoflavones.

* * * * *